(12) United States Patent
Bartlett

(10) Patent No.: US 6,351,988 B1
(45) Date of Patent: Mar. 5, 2002

(54) MEASURING THE ENERGY ABSORBING CAPACITY OF A SUBSTRATE

(75) Inventor: David Ian Bartlett, Shefford (GB)

(73) Assignee: ADAS Consulting Limited, Oxford (GB)

(*) Notice: Subject to any disclaimer, the term of this patent is extended or adjusted under 35 U.S.C. 154(b) by 0 days.

(21) Appl. No.: 09/787,763

(22) PCT Filed: Sep. 17, 1999

(86) PCT No.: PCT/GB99/03098

§ 371 Date: Mar. 22, 2001

§ 102(e) Date: Mar. 22, 2001

(87) PCT Pub. No.: WO00/17622

PCT Pub. Date: Mar. 30, 2000

(30) Foreign Application Priority Data

Sep. 23, 1998 (GB) .............................................. 9820616

(51) Int. Cl.⁷ .................................................. G01N 3/48
(52) U.S. Cl. ........................................................ 73/84
(58) Field of Search ........................... 73/784, 146, 78, 73/81, 82, 84, 85

(56) References Cited

U.S. PATENT DOCUMENTS

| | | | |
|---|---|---|---|
| 2,833,144 A | * | 5/1958 | Miller et al. .................... 73/84 |
| 4,302,967 A | | 12/1981 | Dufey ............................ 73/84 |
| 4,343,179 A | | 8/1982 | Aström et al. ................. 73/81 |
| 4,887,459 A | | 12/1989 | Thomas ......................... 73/81 |
| 5,471,868 A | * | 12/1995 | Nolan ............................ 73/84 |
| 5,726,349 A | | 3/1998 | Palmertree et al. ............. 73/84 |
| 5,831,161 A | | 11/1998 | Johnson et al. ............. 73/432.1 |

FOREIGN PATENT DOCUMENTS

| | | |
|---|---|---|
| BE | 876-648 | 9/1979 |
| GB | 942-614 | 11/1963 |
| GB | 1077097 | 7/1967 |
| GB | 2314636 | 7/1998 |
| WO | 92/10753 | 6/1992 |
| WO | 98/03848 | 1/1998 |

* cited by examiner

*Primary Examiner*—Robert Raevis
(74) *Attorney, Agent, or Firm*—Fleshner & Kim, LLP

(57) ABSTRACT

Apparatus for measuring the energy absorption capacity of a substrate, comprises: a probe (1); means for driving the probe (1) into the substrate so that the probe (1) penetrates the substrate; measuring means (4, 8) arranged to take a plurality of measurements of the force applied to the probe (1) and of the displacement of the probe (1) as the probe (1) penetrates the substrate; and processing means (12) arranged to integrate instantaneous readings of both said measurements to give a measurement of the energy required to drive the probe (1) into the substrate and hence determine a measurement of the energy absorbing capacity of the substrate. A corresponding method is also disclosed.

18 Claims, 3 Drawing Sheets

MEASURING THE ENERGY ABSORBING CAPACITY OF A SUBSTRATE

This application claims priority to PCT/GB99/03098, filed Sep. 17, 1999, which published on Mar. 30, 2000 with Publication No. WO 00/17622 in the English language and which claimed priority to GB Patent Application No. 9820616.2, filed Sep. 23, 1998.

FIELD OF INVENTION

This invention relates to apparatus for, and a method of, measuring the energy absorbing capacity of the surface of a racecourse and, particularly, the application of this to providing a measurement of the "going" of such a racecourse.

BACKGROUND TO THE INVENTION

A large proportion of horse-racing takes place on turf courses.

The "going" of a course varies depending on, among other things, how it has been managed and how wet it is. It is well-known that race times vary depending on the state of the course and that hard ground brings an increased risk of injury to horse and rider. During the run up to race meetings, and at the events themselves, the state of the course is of interest to the racing authorities, trainers, owners, jockeys and punters.

The "going" of a racecourse is traditionally measured by a person pressing a walking stick into the ground and that person making an assessment of the "going", e.g. as "soft", "firm" or "hard" and in some cases seven levels of assessment are given). This assessment is, however, highly subjective, especially on firm ground, and even though such assessments are carried out only by a small number of highly experienced people, it is common for their assessments to vary. Moreover, in many cases, the "going" will be different on different parts of the racecourse.

BE-A-876648 discloses an apparatus for measuring the mechanical characteristics of a body. The apparatus described comprises purely mechanical components and has the disadvantage that it is difficult for it to be used by unskilled operators on racetracks to give repeatable, accurate indications of the prevailing "going" conditions.

GB-A-942614 describes an instrument for the indication of the "going" of racecourses and the like, but this instrument is merely capable of measuring only compressive forces exerted on the racecourse surface and does not allow the user to determine the energy absorption capacity of the surface. Thus, the device disclosed has the disadvantage that accurate measurement of the "going" of racecourses (which more property, requires measurement based upon energy absorption capacity) is not possible.

Further, various other attempts have been made to provide a quantitative measurement of the "going" of a racecourse but the applicants are unaware of any successful and reliable solution to this problem.

Hence, the present invention aims to provide apparatus and a method for providing a quantitative measurement of the energy absorbing capacity of the surface of a racecourse and thus, in particular, accurate and respectable assessment of the "going" of such a racecourse.

SUMMARY OF THE INVENTION

Thus, according to a first aspect of the invention, there is provided apparatus for providing quantitative assessment of the "going" of a racecourse by measuring the mechanical energy absorption capacity of the racecourse surface, comprising: a probe; drive means for automatically driving the probe into the surface so that the probe penetrates the surface; measuring means arranged to take a plurality of measurements of the force applied to the probe and of the displacement of the probe as the probe automatically penetrates the surface; and processing means arranged to integrate instantaneous readings of both said measurements to give a measurement of the mechanical energy required to drive the probe into the surface and hence provide a measurement of the mechanical energy absorbing capacity of the racecourse surface, so as to provide a quantitative assessment of the "going" of the racecourse.

According to a second aspect of the invention, there is provided a method of providing quantitative assessment of the "going" of a racecourse by measuring the mechanical energy absorbing capacity of the racecourse surface comprising the steps of: automatically driving a probe into the surface so the probe penetrates the substrate, taking a plurality of measurements of the force applied to the probe and the displacement of the probe as it penetrates the substrate, and integrating instantaneous readings of both said measurements to provide a measurement of the mechanical energy required to drive the probe into the surface and hence provide a measurement of the mechanical energy absorbing capacity of the substrate, so as to provide a quantitative assessment of the "going" of the racecourse.

The invention also relates to the use of the above described apparatus or method to provide a quantitative assessment of the "going" of a racecourse by measurement of the mechanical energy absorbing capacity of the surface of the racecourse.

Other features of the invention will be apparent from the following description and from the subsidiary claims of the specification.

The invention will now be further described, merely by way of example, with reference to the accompanying drawings, in which:

BEST MODE OF INVENTION

The invention will hereinafter be described in relation to its use in providing a measurement of the "going" of a racecourse, the surface of which comprises turf, which is a very non-homogeneous material, although the invention can also be applied to other types of surface, e.g. bare earth, sand, snow or a synthetic surface (e.g. comprising a mixture of sand and organic or synthetic fibres). However, it will be appreciated that the invention may also be used for measuring the energy absorbing capacity of other sports surfaces, substrates carrying any form of traffic (human, animal or mechanical) or substrates used for any other purpose. The term "racecourse" as used herein includes courses used for training.

A first important feature of the present invention is the use of a measurement of the energy absorbing capacity of a racecourse to provide an assessment of the "going" of the racecourse. As the "going" has, until now, been a subjective assessment, it was first necessary to select a measurement which was capable of reflecting this assessment. A wide variety of parameters could be measured, e.g. the hardness of the ground, its compaction, its stiffness or resilience, its composition, its water content etc, but the measurement of the energy absorbing capacity was selected as this was considered to most closely reflect the work done by a horse's hoof as it moves over the racecourse, and experimental trials have shown that the results provide a good match to the current subjective assessment of the "going" of a racecourse.

The energy absorbing capacity of the substrate may be defined as the energy required to drive the probe into the ground and/or the energy required to subsequently extract the probe from the ground.

Figure 1:
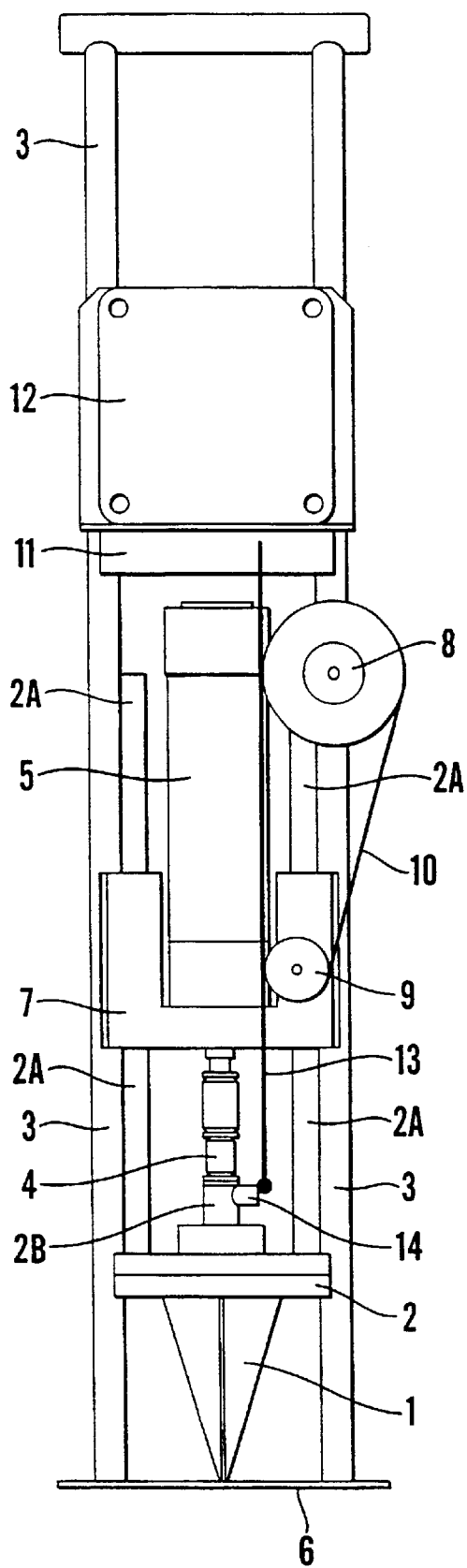
FIG. 1 is a side view of a preferred embodiment of apparatus according to the invention.

The apparatus shown in FIG. 1 comprises a probe 1 in the form of a substantially conical spike with substantially flat wings 2 attached on opposite sides thereof.

The probe 1 is secured to a mounting 2. The mounting 2 is secured to steel guide rails 2A which are slidably mounted within a guide unit 7. The guide unit 7 is rigidly mounted to four steel support rails 3 which are preferably provided at the corners of a square (when the apparatus is viewed from above) although other arrangements would be possible. The mounting of the guide rails 2A within guide unit 7 ensures that the probe can only move axially and cannot be displaced at an angle to the axis thereof. The mounting 2 is also attached by a shaft 2B to drive means in the form of a pneumatic cylinder 5 so that movement of a piston (not shown) within the pneumatic cylinder 5 causes the probe 1 to be moved axially, i.e. up and down in the orientation shown in FIG. 1. The probe 1 can thus be moved so it passes through an aperture in a steel base plate 6 and can be retracted again to the position shown in FIG. 1.

A force transducer 4 is mounted in the connection between the shaft 2B and the pneumatic cylinder to measure the force applied to the probe 1.

A position transducer 8 in the form of a rotary potentiometer is mounted on the apparatus and, in the arrangement shown, measures the axial displacement of the probe 1 by means of a pulley 9, band 10 and linkage rod 13. The linkage rod 13 is rigidly attached to the shaft 2B and to the band 10 so that linear motion of the probe 1 is converted into rotary motion of the potentiometer.

Other types of force and position transducers may be used.

The pneumatic cylinder 5 is controlled by a pneumatic control valve 11, which, in turn, is controlled by an electronic control unit 12.

Figure 2:
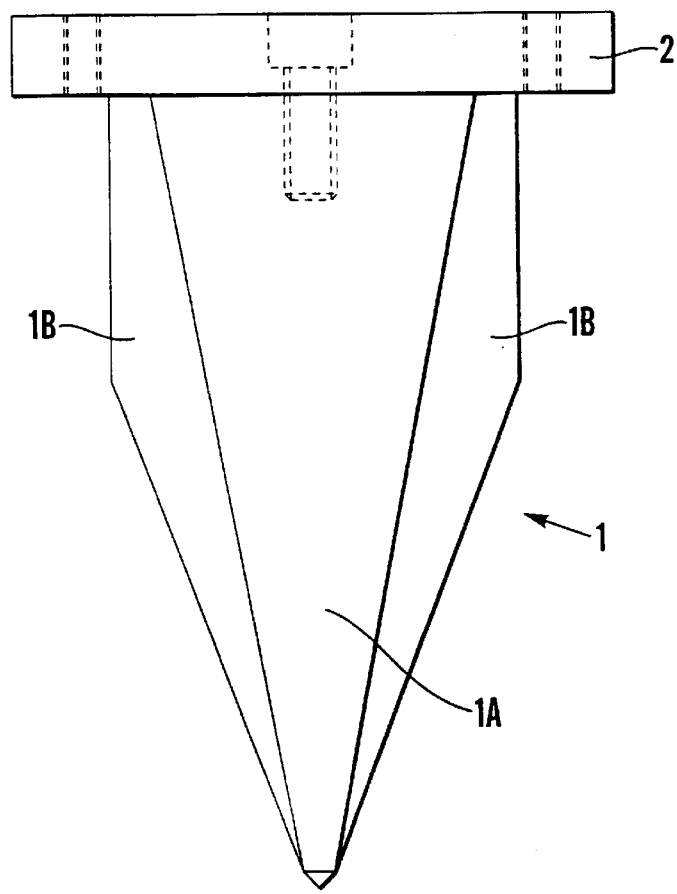
FIGS. 2 and 3 are enlarged, front and bottom views of a preferred form of probe used in the apparatus.
Figure 3:
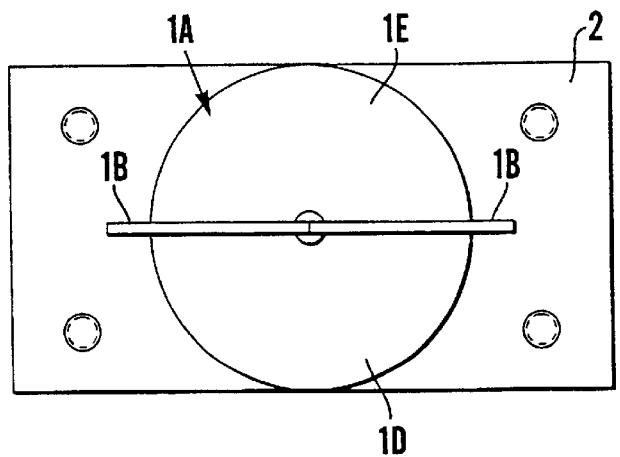

As shown in FIGS. 2 and 3, the probe 1 preferably has a generally conical shape with substantially flat wings 1B on opposite sides thereof. The probe may, for example, comprise a solid steel cone 1A with wings 1B welded to the sides thereof or, as shown in FIG. 3, the wings 1B may comprise a single sheet of steel with two halves 1D and 1E of a cone attached on opposite sides thereof. The wings 1B are substantially co-planar with the axis of the cone. More than two such wings may be provided if required.

In use, the apparatus is positioned with the base plate 6 held in firm contact with the ground. The drive means is then activated so the probe 1 is driven into and penetrates the ground. When the probe 1 stops moving, the drive means is reversed to extract the probe 1 from the ground until it is retracted above to a position above the base plate 6, as shown in FIG. 1. The extent to which the probe penetrates the ground will be determined by the maximum force permitted by the air pressure applied to the pneumatic cylinder and the hardness of the ground.

Whilst the probe 1 is being driven into the ground, and preferably also whilst it is being extracted from the ground, readings are taken either continuously or at frequent intervals from the force transducer 4 and the position transducer 8 by the electronic control unit. In a preferred arrangement readings are taken at the rate of at least 100 samples per second and preferably at least 500 samples per second. In a preferred arrangement, the time taken to drive the probe into the ground is less than one second.

It will be appreciated that by integrating the instantaneous readings from the force transducer 4 and position transducer 8 during the time the probe is penetrating the ground and, again, whilst it is being extracted from the ground, the apparatus is able to measure the energy required to drive the probe into the ground (and, optionally, to extract it again) and thus obtain a measurement of the energy absorbed by the ground during the measurement cycle. Further details of methods of processing the readings taken will be given below.

The apparatus may, optionally, also be provided with an accelerometer 14 to measure the acceleration and/or deceleration of the probe 1. The accelerometer may be mounted on the shaft 2A and readings taken therefrom at similar intervals to the readings from the force transducer 4 and position transducer 8.

The accelerometer is preferably used to determine the maximum deceleration of the probe 1 as it penetrates the ground as it is found that, on some surfaces, e.g. synthetic surfaces comprising a compaction of loose material, this measurement can be used to help differentiate between "firm" and "hard" surfaces. It may also be used to provide a measurement of the hardness (or stiffness) of a surface which can be used to assess whether the surface is safe to use.

The maximum deceleration can be determined by scanning the readings from the accelerometer during the penetration phase of a measurement cycle to locate the maximum reading, or a high speed sample and hold circuit (e.g. 10 KHz) can be used to capture the maximum deceleration.

If an accelerometer is used, the apparatus is preferably arranged so that the tip of the probe is at least 20 mm away from the ground before a measurement cycle is initiated so that the probe has time to accelerate before it engages the ground. The apparatus is thus arranged so that the probe can be retracted to a position at least 20 mm above the base plate 9.

The shape of the probe 1 is designed so that it is sufficiently sharp to penetrate the ground, e.g. to penetrate through thick turf, and it has a conical or tapered shape so that the sides of the probe continue to deform the ground as the probe penetrates the ground. This ensures that useful readings can continue to be taken throughout the vertical extent of the travel of the probe as it penetrates the ground.

The wings 1B provide additional resistance as the probe penetrates the ground and, because they are substantially flat, their sides also remain in contact with ground as the probe is withdrawn so that useful readings can be taken whilst the probe is being extracted from the ground.

In a preferred example of the apparatus, the probe has a length of about 150 mm (from the tip of the case to the base thereof) and the base of the cone has a width of about 60 mm and it has been found that the maximum force required to drive such a probe into dense ground is about 600 N.

The shape of the probe should also be such that it provides useful measurements in a range of different types of ground and over the range of "goings" likely to be encountered.

As mentioned above, the probe is preferably driven through a circular aperture in the base plate 6. The circular aperture preferably has a diameter slightly larger than the combined width of the base of the cone and the wings at the base of the cone, e.g. of about 80 mm. The base plate 6 is in contact with the ground as the probe penetrates the ground and it serves to restrain material displaced by the probe and limits the extent to which this displaced material can rise above ground level. This helps ensure that the ground is deformed in a uniform, controlled manner by the probe 1 so the apparatus provides more consistent and reliable measurements. This arrangement is also beneficial in preventing clods of soil adhering to the probe 1 so reducing the need to clean the probe between measurements.

The force transducer 4 is preferably an electronic analogue force transducer which is arranged to measure both pulling and pushing forces and it is arranged so that it is only subject to axial forces and is not subject to any lateral thrusts.

The electronic control unit 12 is preferably arranged to scan operation of a start switch (not shown) and controls the air supply to the pneumatic cylinder 5. When measurements have been taken, the control unit 12 makes a stepwise integration of the force and position data for penetration and extraction of the probe 1. The upward velocity of the probe is measured at the point when the tip of the probe is passing the ground surface. This velocity is used to compute the kinetic energy which is subtracted from the extraction energy integral to leave only that which is due to the ground condition. These results, together with data on the penetration distance, the penetration and/or extraction time, maximum force and, optionally, the acceleration/deceleration of the probe, are used for further processing, storage and display either by the control unit 12 or by other means connected thereto, e.g. a personal computer (not shown).

The control unit runs a background task that takes the analogue measurements and stores them in a ring buffer. The foregound task manages the start switch, monitors the ring buffer results for the end of penetration and the end of measurement and drives the pneumatic control valves. It also integrates the force and position data and transmits each test result to the attached computer.

The computer receives each test result, scales the measurements into engineering units and updates a user display. The data for each test result is saved in a file.

Once a set of test data has been scaled and its validity checked, it is used to compute a numerical "going" rating. A number of "going" rating s are combined and presented as a measured "going".

Tests with the apparatus have been compared with subjective tests carried out in the manner described above and calibrated in relation thereto. The test results have provided consistent, repeatable readings, which are well-matched to the results of the subjective assessments.

As indicated above, it is found that, in some circumstances, a combination of a measurement of the energy absorption with a measurement of the maximum deceleration of the probe enables the "going", particularly a "firm" to "hard" "going" to be assessed more reliably. Tests have shown that the maximum deceleration on "hard" ground may be around 25 to 30 g, on "good" ground it may be around 2 to 3 g, and on "soft" ground it would be very small, e.g. less than 1 g.

Figure 4:
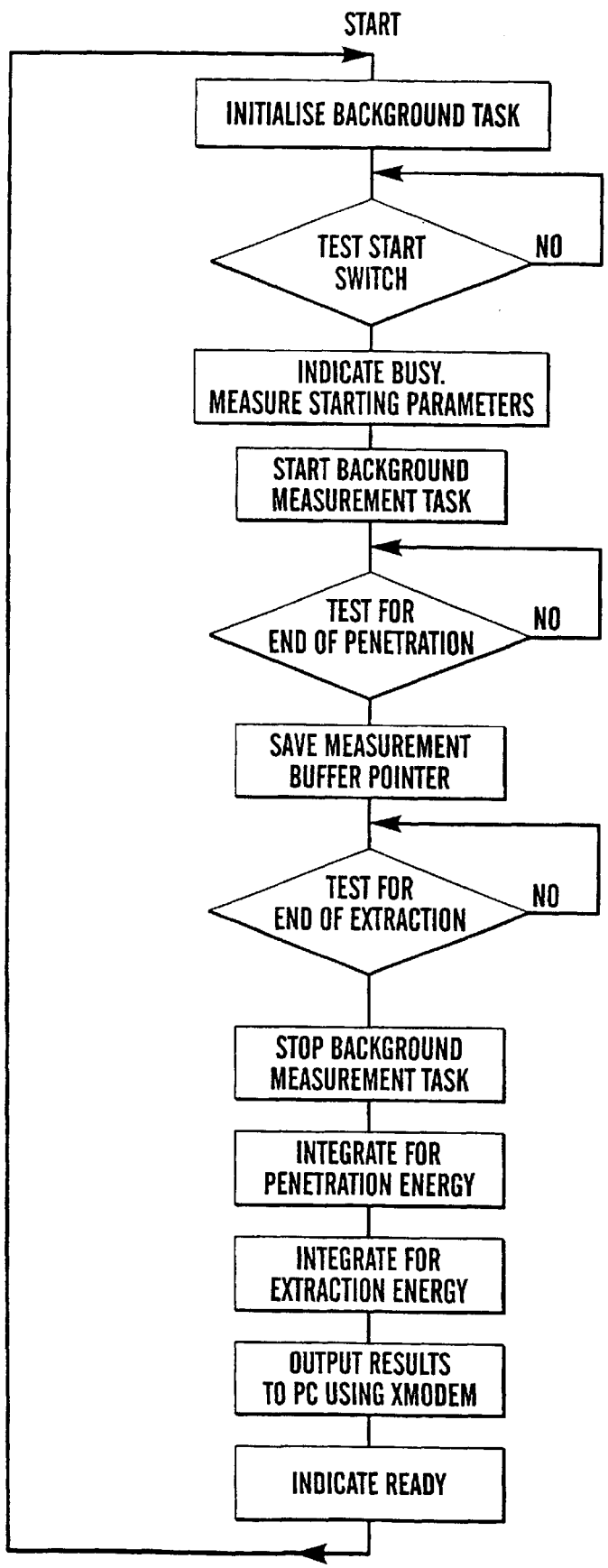
FIG. 4 is a flow diagram of a preferred procedure for carrying out measurements using the apparatus.

FIG. 4 shows a flow chart describing the function of the control unit 12. With the description given above, this flow chart is self-explanatory so will not be described further.

The apparatus described above enables a quantitative measurement of the "going" of a racecourse, which is more repeatable and more reliable than the current subjective assessment. It also enables a finer assessment of the "going" and may, for example, give "going" ratings from 15 (for "heavy") to 85 (for "hard"). Ratings of 15 to 85 may, for example, be given as an assessment of the "going" corresponding to the conventional assessments as follows:

15 to 25 represent a "heavy" going;
25 to 35 represent a "soft" going;
35 to 45 represent a "good to soft" going;
45 to 55 represent a "good" going;
55 to 65 represent a "good to firm" going;
65 to 75 represent a "firm" going; and
75 to 85 represent a "hard" going.

More accurate measurements can be given by numbers within the above ranges, e.g. to indicate that the "going" is towards the hard or soft end of a given rating. This system is thus capable of providing 70 levels of assessment (i.e. the numbers from 15 through 85) ranging from the softest to the hardest "going". Other ranges and forms of calibration may, of course, be used in place of that described above.

What is claimed is:

1. Apparatus for providing a quantitative assessment of the "going" of a racecourse by measuring the mechanical energy absorption capacity of the racecourse surface, comprising: a probe (1); means for automatically driving the probe (1) into the surface of the racecourse o that the probe (1) penetrates the surface; measuring means (4,8) arranged to take a plurality of measurements of the force applied to the probe (1) and of the displacement of the probe (1) as the probe (1) automatically penetrates the surface; and processing means (12) arranged to integrate instantaneous readings of both said measurements to give a measurement of the mechanical energy required to drive the probe (1) into the surface and hence determine a measurement of the mechanical energy absorbing capacity of the racecourse surface, so as to provide a quantitative assessment of the "going" of the racecourse.

2. The apparatus of claim 1, wherein the probe has a substantially conical shape, arranged such that, in use, the narrow end thereof is directed towards the surface.

3. The apparatus of claim 2, wherein the substantially conical probe has at least two substantially planar wings arranged to be co-planar with the axis of the conical probe.

4. The apparatus of claim 1, comprising a plate which is adapted to be holdable in contact with the surface to be tested, the probe being arranged to pass through an aperture in the plate as it is driven into the surface.

5. The apparatus of claim 1, wherein the drive means comprises a pneumatic cylinder.

6. The apparatus of claim 1, wherein the measuring means comprises a force transducer for measuring the force applied to the probe and a position transducer for measuring the displacement of the probe as it is driven into the surface.

7. The apparatus of claim 1, wherein the measuring means is also adapted to measure the force applied to the probe and the displacement of the probe during extraction of the probe from the surface.

8. The apparatus of claim 1, wherein said measurements are measurable as the probe penetrates the surface until the probe stops or until the application of a predetermined level of force to the probe.

9. The apparatus of claim 1, wherein said measurements are continuously measurable during movement of the probe or measurable at frequent intervals, the frequent intervals being one of at least 100 measurements per second and at least 500 measurements per second, during such movement.

10. The apparatus of claim 1, wherein the processing means is arranged to integrate the said measurements to provide a measure of the energy absorbing capacity of the surface.

11. The apparatus of claim 1, wherein the measuring means is arranged to measure one or more of: the distance the probe penetrates the surface, the time taken for the probe to penetrate the surface and/or be extracted therefrom and the maximum force applied to the probe by the driving means.

12. The apparatus of claim 1, wherein the quantitative assessment of the "going" is providable as one of a range of at least 7, and preferably at least 70, levels of assessment ranging from the softest "going" to the hardest "going".

13. The apparatus of claim 1, comprising an accelerometer for measuring the acceleration/deceleration of the probe.

14. The apparatus of claim 13, wherein measurements from the accelerometer are used to determine the maximum deceleration of the probe as it penetrates the surface.

15. The apparatus of claim 14, wherein the measurements of the energy absorbing capacity of the surface and of the maximum deceleration of the probe are combinable to provide the quantitative assessment of the "going" of the racecourse.

16. A method for providing a quantitative assessment of the "going" of a racecourse by measuring the mechanical energy absorbing capacity of the racecourse surface comprising: automatically driving a probe into the surface so the probe penetrates the surface, taking a plurality of measurements of the force applied to the probe and the displacement of the probe as it penetrates the substrate, and integrating instantaneous readings of both said measurements to provide a measurement of the mechanical energy required to drive the probe into the surface and hence provide a measurement of the mechanical energy absorbing capacity of the racecourse surface so as to provide a quantitative assessment of the "going" of the racecourse.

17. The apparatus of claim 16, wherein the measurement of the acceleration/deceleration of the probe are taken and combined with the measurement of the energy absorbing capacity of the surface to provide the quantitative assessment of the "going" of the racecourse.

18. The apparatus of claim 17, wherein the surface of the racecourse comprises turf.

* * * * *